United States Patent
Behrens et al.

(10) Patent No.: US 7,875,653 B2
(45) Date of Patent: Jan. 25, 2011

(54) EMULSION COMPRISING 1,2-ALKANEDIOLS AND POLAR OIL COMPONENTS

(75) Inventors: Svea Behrens, Hamburg (DE); Uta Meiring, Hamburg (DE); Andreas Clausen, Hamburg (DE); Andreas Bleckmann, Ahrensburg (DE); Jens Nielsen, Henstedt-Ulzburg (DE)

(73) Assignee: Beiersdorf AG, Hamburg (DE)

( * ) Notice: Subject to any disclaimer, the term of this patent is extended or adjusted under 35 U.S.C. 154(b) by 779 days.

(21) Appl. No.: 11/585,217

(22) Filed: Oct. 24, 2006

(65) Prior Publication Data

US 2007/0092478 A1  Apr. 26, 2007

(30) Foreign Application Priority Data

Oct. 25, 2005 (DE) ................. 10 2005 051 862

(51) Int. Cl.
  *B01F 3/08* (2006.01)
  *A61K 8/34* (2006.01)
(52) U.S. Cl. ................. 516/21; 514/728; 424/70.31
(58) Field of Classification Search ............... 516/21; 424/70.31
See application file for complete search history.

(56) References Cited

U.S. PATENT DOCUMENTS

| | | | |
|---|---|---|---|
| 5,041,439 A | | 8/1991 | Kasting et al. |
| 6,040,347 A | * | 3/2000 | Cupferman et al. ......... 514/723 |
| 6,123,953 A | | 9/2000 | Greff |
| 6,274,124 B1 | | 8/2001 | Vollhardt |
| 6,653,397 B2 | | 11/2003 | Bleckmann et al. |
| 6,793,929 B2 | | 9/2004 | Bleckmann et al. |
| 6,936,265 B2 | | 8/2005 | Bleckmann et al. |
| 7,138,128 B2 | | 11/2006 | Bleckmann et al. |
| 2002/0082327 A1 | | 6/2002 | Bleckmann et al. |
| 2002/0102282 A1 | | 8/2002 | Bleckmann et al. |
| 2002/0106386 A1 | | 8/2002 | Bleckmann et al. |
| 2002/0146438 A1 | | 10/2002 | Bleckmann et al. |
| 2003/0017176 A1 | | 1/2003 | Bleckmann et al. |
| 2003/0195263 A1 | | 10/2003 | Schmaus et al. |
| 2005/0013781 A1 | * | 1/2005 | Dueva-Koganov et al. .... 424/59 |
| 2005/0032916 A1 | | 2/2005 | Deckner |
| 2005/0058679 A1 | | 3/2005 | Kropke et al. |
| 2005/0222276 A1 | * | 10/2005 | Schmaus et al. ............ 514/738 |
| 2005/0232953 A1 | * | 10/2005 | Barnikol et al. ............. 424/400 |
| 2005/0238605 A1 | * | 10/2005 | Kohlhase et al. ......... 424/70.13 |
| 2007/0041916 A1 | | 2/2007 | Kropke et al. |

FOREIGN PATENT DOCUMENTS

| | | |
|---|---|---|
| DE | 19855153 | 5/2000 |
| DE | 19924277 | 11/2000 |
| DE | 10019210 | 10/2001 |
| DE | 10048125 | 4/2002 |
| DE | 10048366 | 4/2002 |
| DE | 10048427 | 4/2002 |
| DE | 10048429 | 4/2002 |
| DE | 10048683 | 4/2002 |
| DE | 10226990 | 3/2004 |
| DE | 10341179 | 3/2005 |
| EP | 0249397 | 12/1987 |
| EP | 0655904 | 6/1995 |
| EP | 1078638 | 2/2001 |
| EP | 1426029 | 6/2004 |
| WO | 03/000220 | 1/2003 |
| WO | 03/066012 | 8/2003 |
| WO | 03/069994 | 8/2003 |
| WO | 2004/050045 | 6/2004 |
| WO | 2005/016292 | 2/2005 |

OTHER PUBLICATIONS

"Functional Isodragol" internet download from http://www.symrise.com/fileadmin/user_upload/pdf/Isodragol.pdf.*
"Functional PCL-Liquid", download from internet http://www.symrise.com/fileadmin/user_upload/pdf/PCL-Liquid.pdf.*
"Lanette 18 Data" download from internet http://www.products.cognis.com/cognis/prodleaf.nsf/($ProductsbyDocID_PL-Header)/REF85ECC97F18AFC19C4125693D004DD9CE/$file/LANETTE_r_18_E.pdf.*
Dow Coring 200 Fluid product information download from internet http://www.polysi.com/dow%20corning%20msds%20sheets/DC%20Tech%20&%20MSDS%20Sheets/DC%20FLUIDS%20TECH%20SHEETS/DC%20200%20600000cst.pdf.*
English Language Abstract of WO 95/01151.
English Language Abstract of DE 1 598 064.
English Language Abstract of EP 1 147 760, Oct. 24, 2001.
English Language Abstract of DE 100 48 427, Apr. 11, 2002.
English Language Abstract of DE 100 48 429, Apr. 11, 2002.
U.S. Appl. No. 11/585,244, filed Oct. 24, 2006 and entitled "Cosmetic O/W emulsion comprising 1,2-hexanediol".
U.S. Appl. No. 11/585,246, filed Oct. 24, 2006 and entitled "Cosmetic preparation with 1,2-alkanediol and triazines".

* cited by examiner

*Primary Examiner*—Ling-Siu Choi
*Assistant Examiner*—Chun-Cheng Wang
(74) *Attorney, Agent, or Firm*—Greenblum & Bernstein, P.L.C.

(57) ABSTRACT

An emulsion comprising (a) more than about 40% by weight, based on the total weight of the lipid phase of the emulsion, of one or more polar and/or moderately polar lipids which exhibit an interfacial tension towards water of less than about 30 mN/m and (b) one or more 1,2-alkanediols having about 4 to about 8 carbon atoms and exhibiting a Ig $p_{ow}$ of from about −1 to about +3. This Abstract is not intended to define the invention disclosed in the specification, nor intended to limit the scope of the invention in any way.

20 Claims, No Drawings

EMULSION COMPRISING 1,2-ALKANEDIOLS AND POLAR OIL COMPONENTS

CROSS-REFERENCE TO RELATED APPLICATIONS

The present application claims priority under 35 U.S.C. §119 of German Patent Application No. 10 2005 051 862.1, filed Oct. 25, 2005, the disclosure of which is expressly incorporated by reference herein in its entirety.

BACKGROUND OF THE INVENTION

1. Field of the Invention

The present invention relates to emulsions as cosmetic preparations which comprise 1,2-alkanediols and polar oil components. The compositions according to the present invention exhibit good sensory properties that result, among others, in improved in-vivo effectiveness.

2. Discussion of Background Information

The skin is our largest organ and at the same time the reflection of our soul. No other organ is so exposed to outside influences. Heat, cold or solar radiation, wrong or excessive cleansing of the skin, all of this stresses the skin.

Every day water evaporates via the surface of the skin. Internal and external factors additionally influence the degree of drying, such as hormonal influences, biological aging, disease and nutrition, light, environment and climate.

Normal skin and especially dry skin must therefore be supplied with moisture, lipids and optionally active ingredients. Healthy skin has different possibilities for keeping water loss to a minimum. It has so-called humectant factors, namely salts, various organic acids and urea. These factors take on the function of binding moisture and retaining it in the skin. The skin fats, lipids, are just as important. Only with the aid of this intact protective barrier is it possible for the upper layer of the skin to regulate the water content and additionally to ensure that infective agents such as bacteria, viruses or fungi and other harmful substances cannot penetrate the skin unhindered.

Dry skin is sensitive and mainly needs care. Cosmetic preparations such as creams and lotions primarily have the function of sustainably balancing the fat and moisture requirements of the skin, thus reestablishing the natural balance in the skin. It is therefore important to use preparations that contain in equal measure the skin-related lipids, humectants and active care ingredients. In addition, a care product also needs active ingredients that are able to bind water in the skin in the long term.

Lipids are fats and fatty substances. For cosmetics they are important primarily as emollient ingredients and as lipids that are present in the horny layer of the epidermis and that are stored between the horny cells. They enable the skin to store moisture. In addition to the skin care aspect, lipids are added to the cosmetic preparations in order to ensure it is easier to disperse them on the skin and in order to improve the sensory properties of the preparations.

As used in the present specification and the appended claims, the term "lipids" is used as a generic term for fats, oils, waxes and the like, said term being entirely commonplace to a person of skill in the art. Further the terms "oil phase" and "lipid phase" are used herein interchangeably.

Oils and fats differ from one another in their polarity, which is difficult to define. It has already been proposed to adopt the interfacial tension towards water as a measure of the polarity index of an oil or of an oil phase. The lower the interfacial tension between this oil phase and water, the greater the polarity of the oil phase in question. According to the present invention, the interfacial tension is regarded as one possible measure of the polarity of a given oil component.

The interfacial tension is the force which acts on an imaginary line one meter in length at the interface between two phases. The physical unit for this interfacial tension is conventionally calculated from the force/length relationship and is usually expressed in mN/m (millinewtons divided by meters). It has a positive sign if it tends to reduce the interface. In the converse case, it has a negative sign. For the purposes of the present invention, lipids are regarded as polar if their interfacial tension towards water is less than about 20 mN/m, and as nonpolar if their interfacial tension towards water is more than about 30 mN/m. Lipids with an interfacial tension towards water between about 20 and about 30 mN/m are generally referred to as moderately polar.

EP 655904 generally describes the use of alkane diols with 5 to 10 carbon atoms in cosmetic products and in particular their skin-moisturizing effect.

DE 10341179 discloses deodorant compositions with a combination of alkane-1,2-diols and α- and/or β-hydroxyacids. The antibacterial effect of alkane-1,2-diols is also known. JP 2002/2003330 thus describes the antibacterial effect of a combination of alkane-1,2-diols and ascorbic acid esters. WO 03/000220 describes the use of 1,2-decanediol against bacteria causing body odor. U.S. Pat. No. 6,123,953 describes the use of alkane-1,2-diols for inactivating skin microorganisms by the use of 1,2-octanediol.

Emulsions, here in particular W/O, O/W or W/O/W emulsions, are often used as cosmetic or medical preparations. Emulsions are generally understood as meaning heterogeneous systems which comprise two liquids which are immiscible or only miscible with one another to a limited extent, which liquids are normally referred to as phases. In an emulsion, one of the two liquids (W/O) is dispersed in the other liquid in the form of very fine droplets.

If the two liquids are water and oil and if oil droplets are finely distributed in water, then this is an oil-in-water emulsion (O/W emulsion, e.g., milk). The basic character of an O/W emulsion is determined by the water. In the case of a water-in-oil emulsion (W/O emulsion, e.g., butter), the principle is reversed, the basic character here being determined by the oil.

One skilled in the art is naturally aware of a plurality of possibilities for formulating stable emulsion preparations for cosmetic or dermatological application, e.g., in the form of creams and ointments that are spreadable in the range of room temperature to skin temperature, or as lotions and milks, that are rather flowable in this temperature range.

A plurality of lipids are known from DE 1001921 that as an addition to W/O emulsions have better sensory properties, such as, e.g., ease of distribution on the skin or the ability to be absorbed by the skin.

However, the problem with all the preparations is to produce stable emulsions with a predominantly polar oil phase without any losses in terms of sensory properties.

In the prior art, attempts to solve this problem of the interfacial activity of the lipids are made by adding suitable thickener systems, which, in turn, results in the referenced disadvantages in terms of the sensory properties of the cosmetic preparation.

Thus in DE 198 55 153, DE 199 24 277, DE 100 48 125, DE 100 48 366, DE 100 48 427, DE 100 48 429 and in DE 100 48 683 it is mentioned that preparations in combination with very polar oils, such as, e.g., the vegetable oils which are frequently used in commercial products, have the disadvantage that they are unstable or are limited to a narrow field of application or to a very limited selection of materials.

It would be advantageous to have available stable emulsions and in particular cosmetic preparations that contain predominantly polar oil components.

SUMMARY OF THE INVENTION

The present invention provides an emulsion which comprises (a) more than about 40% by weight, based on the total weight of the lipid phase of the emulsion, of one or more lipids which are polar and/or moderately polar and exhibit an interfacial tension towards water of less than about 30 mN/m and (b) one or more 1,2-alkanediols which comprise from about 4 to about 8 carbon atoms and exhibit a lg $p_{ow}$ of from about −1 to about +3.

In one aspect of the emulsion of the present invention, the one or more 1,2-alkanediols may exhibit a lg $p_{ow}$ of from about −1 to about +1. In another aspect, they may comprise 1,2-hexanediol, optionally in combination with methylpropanediol and/or ethylhexyl glycerin.

In another aspect, the emulsion of the present invention may comprise more than about 40% by weight, based on the total weight of the lipid phase, of one or more lipids which exhibit an interfacial tension towards water of less than about 20 mN/m.

In yet another aspect, the emulsion may comprise both polar lipids and moderately polar lipids.

In a still further aspect, the emulsion may comprise more than about 25% by weight, e.g., more than about 40% by weight, based on the total weight of the lipid phase, of one or more polar lipids.

In another aspect of the emulsion of the present invention, component (a) thereof may comprise one or more lipids selected from cocoglycerides, caprylic/capric triglycerides, octyldodecanol and isopropyl palmitate. Further, component (a) may further comprises dimethicone.

In another aspect, the emulsion of the present invention may comprise an O/W emulsion. For example, the O/W emulsion may comprise one or more O/W emulsifiers selected from glyceryl stearate citrate, polyglyceryl methyl glucose distearate and polyethylene glycol(2000) monostearate.

The present invention also provides an emulsion which comprises (a) more than about 40% by weight, based on the total weight of a lipid phase of the emulsion, of at least one polar lipid and at least one moderately polar lipid, which lipids exhibit an interfacial tension towards water of less than about 30 mN/m and (b) one or more 1,2-alkanediols which comprise about 4 to about 8 carbon atoms, exhibit a lg $p_{ow}$ of from about −1 to about +1, and comprise 1,2-hexanediol.

In one aspect of this emulsion, the emulsion may further comprise ethylhexyl glycerin.

In another aspect, the emulsion may comprise more than about 40% by weight, based on the total weight of the lipid phase, of one or more polar lipids and/or more than about 40% by weight, based on the total weight of the lipid phase, of one or more lipids which exhibit an interfacial tension towards water of less than about 20 mN/m.

In another aspect, component (a) of the emulsion of the present invention may comprise one or more of lipids selected from cocoglycerides, caprylic/capric triglycerides, octyldodecanol and isopropyl palmitate.

The present invention also provides a cosmetic preparation which comprises the emulsion of the present invention as set forth above, including the various aspects thereof. For example, the preparation may be present as a cream, a lotion or a pump spray.

The present invention also provides a method of producing a cosmetic preparation which comprises a predominantly polar lipid phase and exhibits long-term stability, wherein the method comprises incorporating into the preparation the emulsion of the present invention as set forth above, including the various aspects thereof.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

lg $p_{ow}$ is the logarithmic $K_{ow}$, 1-octanol-water distribution coefficient. An abbreviation for the 1-octanol/water distribution coefficient, this is the ratio between the concentrations of a substance in the two phases 1-ocanol (nonpolar) and water (polar) stable. $p_{ow}$ increases with increasing liposolubility and decreasing water-solubility. The larger the $p_{ow}$, the more readily a bioaccumulation can take place in body fats (membranes, storage fat). However, with very high $p_{ow}$ (lg $p_{ow}$>about 6.5) a decrease in the bioaccumulation tendency is frequently observed.

Alkane-1,2-diols with an lg $p_{ow}$ in the range of from about −1 to about +1, are particularly advantageous since alkane diols in this preferred lg $p_{ow}$ range exhibit a balanced distribution between the water/oil interface and thus contribute to interface stabilization.

Polar oils with an interfacial tension towards water of less than about 20 mN/m are particularly preferred. Non-limiting examples of such polar oils include lecithins and the fatty acid triglyerides, particularly the triglycerin esters of saturated and/or unsaturated, branched and/or unbranched alkanecarboxylic acids having a chain length of from about 8 to about 24 carbon atoms, e.g., from about 12 to about 18 carbon atoms. The fatty acid triglycerides can be advantageously chosen, e.g., from synthetic, semi-synthetic and naturally occurring oils, for example olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil and the like, as well as from jojoba oil waxes.

Particularly advantageous polar lipids within the scope of the present invention are all native lipids, such as, e.g., olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil, corn oil, avocado oil and the like as well as those listed below.

| Trade Name | INCI Name | Polarity [mN/m] |
|---|---|---|
| Isofol 14 T | Butyl decanol (+) hexyl octanol (+) Hexyl decanol (+) butyl octanol | 19.8 |

-continued

| Trade Name | INCI Name | Polarity [mN/m] |
|---|---|---|
| Lipovol MOS-130 | Tridecyl stearate (+) tridecyl trimellitate (+) Dipentaerythrityl hexacaprylate/hexacaprate | 19.4 |
| Castor oil | | 19.2 |
| Isofol Ester 0604 | | 19.1 |
| Miglyol 840 | Propylene glycol dicaprylate/dicaprate | 18.7 |
| Isofol 12 | Butyl octanol | 17.4 |
| Tegosoft SH | Stearyl heptanoate | 17.8 |
| Avocado oil | | 14.5 |
| Cetiol B | Dibutyl adipate | 14.3 |
| Dermol 488 | PEG 2 Diethylene hexanoate | 10.1 |
| Cosmacol ELI | C12-13 Alkyl lactate | 8.8 |
| Dermol 489 | Diethylene glycol dioctanoate (/diisononanoate) | 8.6 |
| Cosmacol ETI | Di-C12/13 Alkyl tartrate | 7.1 |
| Emerest 2384 | Propylene glycol monoisostearate | 6.2 |
| Myritol 331 | Cocoglycerides | 5.1 |
| Prisorine 2041 GTIS | Triisostearin | 2.4 |

In addition to the substances described as polar lipids or oil components, however, moderately polar lipids (i.e., lipids of medium polarity) are also preferred. Moderately polar lipids have an interfacial tension towards water between about 20 and about 30 mN/m.

The moderately polar lipid phase advantageously comprises lipids that are chosen from dialkyl ethers and saturated or unsaturated, branched or unbranched alcohols. It is in particular advantageous if the oil phase comprises $C_{12\text{-}15}$ alkyl benzoate.

In addition, components of the oil phase can advantageously be chosen from Guerbet alcohols. Guerbet alcohols are named after Marcel Guerbet who described their preparation for the first time. They are formed according to the equation

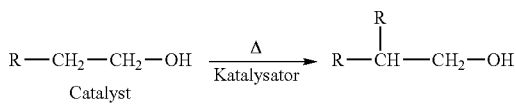

by oxidation of an alcohol into an aldehyde, by aldol condensation of the aldehyde, elimination of water from the aldol and hydrogenation of the allyl aldehyde. Guerbet alcohols are liquid even at low temperatures and cause virtually no skin irritations. They can be used advantageously as fatting, superfatting and also refatting constituents in skin care and hair care compositions.

The use of Guerbet alcohols in cosmetics is known per se. Such species in most cases are of the structure

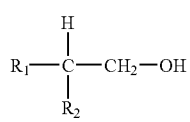

wherein $R_1$ and $R_2$ are usually unbranched alkyl radicals.

According to the present invention, the Guerbet alcohol(s) is/are advantageously chosen from $R_1$=propyl, butyl, pentyl, hexyl, heptyl or octyl and $R_2$=hexyl, heptyl, octyl, nonyl, decyl, undecyl, dodecyl, tridecyl or tetradecyl.

Guerbet alcohols which are preferred according to the present invention include 2-butyloctanol of the structure

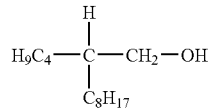

which is available, for example, under the trade name Isofol® 12, and 2-hexyldecanol of the structure

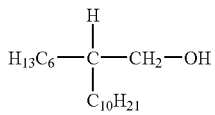

which is available, for example, under the trade name Isofol® 16. Mixtures of Guerbet alcohols can also be used advantageously. Mixtures of 2-butyloctanol and 2-hexyldecanol are available, for example, under the trade name Isofol® 14.

Any mixtures of such oil and wax components can also be used advantageously for the purposes of the present invention. It may also be advantageous to use waxes, for example cetyl palmitate, as a component of the oil phase.

Particularly advantageous moderately polar lipids for the purposes of the present invention include the substances listed below:

| Trade Name | INCI Name | Polarity [mN/m] |
|---|---|---|
| DUB VCI 10 | Isodecyl neopentanoate | 29.9 |
| Dermol IHD | Isohexyl decanoate | 29.7 |
| Dermol 108 | Isodecyl octanoate | 29.6 |
| Dihexyl ether | Dihexyl ether | 29.2 |
| Dermol 109 | Isodecyl 3,5,5-trimethyl hexanoate | 29.1 |
| Cetiol SN | Cetearyl isononanoate | 28.6 |
| Isopropyl palmitate | Isopropyl palmitate | 28.8 |
| Jojobaoel Gold | | 26.2 |
| Wacker AK 100 | Dimethicone | 26.9 |
| Dermol 98 | 2-Ethylhexanoic acid 3,5,5 trimethyl ester | 26.2 |
| Eutanol G | Octyldodecanol | 24.8 |
| Isofol 16 | Hexyl decanol | 24.3 |
| Dermol 139 | Isotridecyl 3,5,5 trimethyl hexanonanoate | 24.5 |
| Cetiol PGL | Hexyldecanol (+) hexyl decyl laurate | 24.3 |
| Cegesoft C24 | Octyl palmitate | 23.1 |
| M.O.D. | Octyldodecyl myristate | 22.1 |
| Macadamia Nut Oil | | 22.1 |
| Silicone oil VP 1120 | Phenyl trimethicone | 22.7 |
| Isocarb 12 | Butyl octanoic acid | 22.1 |
| Isopropyl stearate | Isopropyl stearate | 21.9 |
| Finsolv TN | $C_{12\text{-}15}$ Alkyl benzoate | 21.8 |
| Dermofeel BGC | Butylene glycol caprylate/caprate | 21.5 |
| Miglyol 812 | Caprylic/capric triglyceride | 21.3 |
| Trivent OCG | Tricaprylin | 20.2 |
| Dermol 866 | PEG Diethylhexanoate/diisononanoate/ethylhexyl isononanoate | 20.1 |

In particular lipids from the group of triglycerides, such as, e.g., caprylic capric, and Guerbet alcohols, such as, e.g., octyldodecanol may advantageously be used as moderately polar lipids.

Furthermore, isodecyl neopentanoate, isopropyl palmitate and isopropyl stearate and $C_{12-15}$ alkyl benzoate are examples of lipids which are particularly advantageous.

The moderately polar lipids are usually present in the formulation in a total amount of from about 5% to about 20% by weight, preferably from about 7% to about 15% by weight, based on the total weight of the entire lipid phase.

Emulsions which comprise both moderately polar lipids and polar lipids are particularly preferred.

The polar lipids usually account for at least about 25% by weight, preferably at least about 40% by weight, of the total weight of the lipid phase of the emulsion of the present invention.

Cocoglycerides (polar) and caprylic/capric triglycerides, octyldodecanol and isopropylpalmitate, optionally in combination with dimethicone (moderately polar) are preferred according to the present invention, since due to their physio-chemical properties, these lipids in combination exhibit a balanced profile on the skin in sensory terms.

The use of the 1,2-alkanediols comprising from about 4 to about 8 carbon atoms and an Ig $p_{ow}$ of from about −1 to about +3, advantageously from about −1 to about +1, in combination with polar and/or moderately polar lipids makes it possible to provide emulsions that comprise a predominantly polar lipid phase with long-term stability without a negative influence on the cosmetic formulation in sensory terms occurring thereby. The term "long-term stability" as used herein means stability for about 6 months at 40° C. and/or for about 2.5 years at room temperature.

The use of the emulsion according to the present invention for producing cosmetic preparations with long-term stability which comprise a predominantly polar lipid phase, i.e., more than about 40% by weight of polar and/or moderately polar lipids, preferably polar lipids, has thus become possible for the first time.

Sensory data are surveyed as a standard feature in the Sensory Research Panel (SRU-Panel). Polar lipid components such as, e.g., avocado oil have a high protective and care function due to their richness, which on the one hand is desirable, but has a negative impact in the formulation on the emulsion stability. Oil separation and/or water separation therefore sometimes occur. Through the addition of 1,2-alkanediols the stability can be considerably improved (e.g., about 6 months at 40° C.) and the sensory impression of the produced emulsions has a more balanced sensory profile, i.e., an improved absorption and ease of distribution with the same protective and care capacity.

Cosmetic and dermatological preparations according to the present invention can be provided in various forms. Thus, for example, they may be an emulsion or a microemulsion of the water-in-oil (W/O) type, a multiple emulsion, for example, of the water-in-oil-in-water (W/O/W) type, an emulsion of the oil-in-water (O/W) type, or a gel emulsion or hydrodispersion gel. Cosmetic preparations in the form of oil-in-water (O/W) emulsions are particularly advantageous according to the present invention.

Preferred O/W emulsifiers for use in the emulsions according to the present invention include one or more of glyceryl stearate citrate (CAS 39175-72-9, INCI glyceryl stearate citrate, e.g., Imwitor 370 from Hüls), polyglyceryl methylglucose distearate (INCI polyglyceryl methyl glucose distearate, e.g., Tego Care 450 from Goldschmidt) and polyethylene glycol(2000) monostearate (INCI PEG-40 stearate).

Optionally, the aqueous phase of the emulsion-based preparations advantageously comprises alcohols, diols and/or polyols having a low carbon number, and/or ethers thereof, preferably ethanol, isopropanol, propylene glycol, glycerin, ethylene glycol, ethylene glycolmonoethyl- or -monobutylether, propylene glycol monomethyl, monoethyl or monobutylether, diethylene glycolmonomethyl or monoethylether and analogous products, also alcohols having a lower carbon number, e.g., ethanol, isopropanol, 1,2-propane diol, glycerin.

A particular advantage of the present invention is that it usually makes it possible to use high contents of polyols, in particular glycerin, i.e., from about 3% to about 30% by weight, preferably from about 5% to about 25% by weight and particularly preferably from about 7.5% to about 15% by weight, based on the total weight of the preparation.

Emulsions according to the present invention preferably comprise one or more hydrocolloids.

An advantage of cosmetic preparations containing cosmetic or dermatological active ingredients, preferably antioxidants, is that they can protect the skin from oxidative, photochemical and/or radical stress.

Further particularly advantageous active ingredients for the purposes of the present invention include natural active ingredients and/or derivatives thereof, such as, for example, alpha-lipoic acid and derivatives thereof, phytoene, ursolic acid, sericosides, D-biotin, coenzyme Q10 (ubiquinone or ubiquinol and derivatives thereof, alpha-glucosylrutin, carnitine, carnosine, natural and/or synthetic isoflavonoids, creatine, taurine and/or β-alanine, and 8-hexadecene-1,16-dicarboxylic acid (dioic acid, CAS number 20701-68-2; provisional INCI name octadecenedioic acid).

The use of the cosmetic preparations according to the present invention for the prophylaxis and treatment of the symptoms of aging skin, for preventing and reducing the development and spread of small lines and wrinkles and for the treatment and care of aged skin also is within the scope of the present invention. Suitable active ingredients for these applications include: ubiquinone, ubiquinol, retinol or derivatives thereof, dehydroepiandrosterone (DHEA), isoflavonoids, in particular genistein and daidzein, creatine, phytoestrogens, niacinamide and/or polyphenols (alpha-glucosylrutin).

Furthermore, the use of the cosmetic preparations according to the present invention for the prophylaxis and treatment of the symptoms of dry skin is also preferred. Suitable additional active substances for this application include: natural oils (sunflower oil, evening primrose oil, jojoba oil, macadamia nut oil, castor oil), ceramides, in particular ceramides I, III and VI, cholesterol, phytosterols, carnitine and derivatives thereof, urea, polyols such as glycerin, pseudoceramides, taurine, fatty alcohols and waxes.

It is known to one skilled in the art that cosmetic formulations are usually inconceivable without the customary auxiliaries and additives. Accordingly the cosmetic and dermatological preparations can also contain cosmetic auxiliaries such as are customarily used in such preparations, for example, builders, fillers, preservatives, perfumes, substances for preventing foaming, dyestuffs, pigments that have a coloring effect, thickeners, surfactants, emulsifiers, moisturizing and/or humectant substances, anti-inflammatory substances, additional active compounds such as vitamins or proteins, light protection agents, insect repellents, bactericides, virucides, water and substances having an antimicrobial, proteolytic or keratolytic action or other conventional constituents of a cosmetic or dermatological formulation such as alcohols, polyols, polymers, foam stabilizers and/or organic solvents.

It is likewise advantageous to use the preparations according to the present invention as sunscreen agents. Accordingly, the preparations for the purposes of the present invention preferably comprise at least one UV-A, UV-B and/or broadband filter substance. The formulations may optionally also comprise one or more organic and/or inorganic pigments as UV filter substances which can be present in the water phase and/or the oil phase.

Further advantageous substances for the care of the skin or the hair include, e.g., moisturizing and humectant agents (so-called moisturizers). For the purposes of the present invention substances chosen from, for example, glycerin, butylene glycol, propylene glycol, biosaccaride gum-1, glycine soya, ethylhexyloxy glycerol, pyrrolidonecarboxylic acid and urea are therefore advantageously added to the emulsion or preparation. In addition, it is particularly advantageous to use polymeric moisturizers selected from water-soluble and/or water-swellable and/or water-gellable polysaccharides. Of particular advantage are, for example, hyaluronic acid, chitosan, or a fucose-rich polysaccharide, which is registered in Chemical Abstracts under the registry number 178463-23-5 and is available, for example, under the trade name Fucogel® 1000.

It is optionally possible and advantageous to use the preparations according to the present invention as a basis for pharmaceutical formulations.

Possible forms of application for the preparations according to the present invention include creams, ointments, hydrodispersions, lotions, tinctures, pump sprays, aerosol sprays, aqueous solutions, cleansing substrates and the like.

Preferred is an application in the form of a cream, a lotion or a pump spray, to a limited extent also in the form of a facial toner.

The cosmetic preparations according to the present invention generally show a profile on the skin that is balanced in sensory terms, i.e., they exhibit an improved absorption and ease of distribution with the same protective and care capacity as comparable emulsions of the prior art (SRU Panel).

Various preparations according to the present invention and the use thereof are presented in the following examples. The indicated proportions are percentages by weight relative to the total weight of the preparation, unless stated otherwise.

EXAMPLES

| | Example No. | | | | | | | |
|---|---|---|---|---|---|---|---|---|
| | 1 Cream | 2 Lotion | 3 Lotion | 4 Cream | 5 Cream | 6 Cream | 7 Lotion | 8 Spray |
| Glyceryl stearate citrate | | 1.0 | | 2.0 | | | | 2.0 |
| PEG-40 Stearate | 1.0 | | | | | 1.5 | | |
| Polyglyceryl methylglucose distearate | | | 2.0 | | 3.0 | | 1.5 | 0.5 |
| Glyceryl stearate | 1.5 | | | | | 1.5 | | |
| Cetyl alcohol | | 0.5 | | 2.0 | 1.5 | 0.75 | 1.0 | |
| Stearyl alcohol | | 0.5 | 0.5 | | | 0.75 | | |
| Cetearyl alcohol | 2.0 | | | | | | | 1.5 |
| Caprylic/capric triglyceride | 5.0 | 4.0 | | 5.0 | | 6.0 | 3.0 | 0.5 |
| Ethylhexylcocoate | | | 2.0 | | | | 1.0 | |
| Octyldodecanol | | 1.0 | 3.0 | | 5.0 | | 2.0 | |
| Dibutyl adipate | 2.0 | | 1.0 | 2.0 | | | 3.5 | |
| Cyclomethicone | 2.0 | | | | | 3.0 | | |
| Dimethicone | 1.0 | | | | | | | 1.5 |
| Dicaprylyl carbonate | | 2.0 | | | 2.0 | | | 3.5 |
| Cocoglycerides | | 3.0 | 1.5 | | 2.0 | 5.0 | | 1.0 |
| Natural oils (e.g., jojoba oil/sunflower oil) | 1.5 | | 3.0 | 0.5 | 1.0 | | 2.0 | 2.5 |
| 1,2-Hexanediol | 0.5 | 0.75 | 2.0 | 0.3 | 1.0 | 1.2 | 0.5 | 0.75 |
| Trisodium EDTA | 0.2 | 0.1 | | 0.05 | | 0.1 | 0.3 | |
| Iminodisuccinate | 0.1 | | 0.1 | | 0.3 | | | 0.5 |
| Phenoxyethanol | 0.3 | 0.1 | | 0.5 | 0.7 | | | 0.4 |
| Parabens | 0.4 | | 0.3 | | 0.3 | | 0.2 | |
| Hexamidine diisethionate | | 0.1 | | | 0.05 | | 0.1 | |
| Imidodiazolidinyl urea | | | | | | | 0.2 | 0.2 |
| DMDM hydantoin | | | 0.2 | | | 0.1 | | |
| Iodopropynyl butyl carbamate | | | | 0.2 | | | 0.05 | |
| Glycerin | 10.0 | 3.0 | 7.0 | 8.0 | 15.0 | 20.0 | 0.5 | 2.0 |
| Tocopheryl acetate | 0.2 | 0.5 | 0.75 | | | 0.3 | | 1.0 |
| Alcohol denat. | 5.0 | 2.5 | | | | 7.5 | | 7.5 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. An emulsion for making a cosmetic preparation, wherein the emulsion comprises (a) more than about 40% by weight, based on a total weight of a lipid phase of the emulsion, of at least one polar lipid and at least one moderately polar lipid which exhibit an interfacial tension towards water of less than about 30 mN/m, (b) one or more 1,2-alkanediols having from about 4 to about 8 carbon atoms and exhibiting an lg $p_{ow}$ of from about −1 to about +3, and (c) from 0.5% to about 30% by weight of one or more polyols, the emulsion being different from a microemulsion and being an oil-in-water (O/W) emulsion, a water-in-oil (W/O) emulsion or a water-in-oil-in-water (W/O/W) emulsion.

2. The emulsion of claim 1, wherein the one or more 1,2-alkanediols exhibit an lg $p_{ow}$ value of from about −1 to about +1.

3. The emulsion of claim 1, wherein (b) comprises 1,2-hexanediol.

4. The emulsion of claim 3, wherein the emulsion further comprises ethylhexyl glycerin.

5. The emulsion of claim 1, wherein the emulsion comprises more than about 40% by weight, based on the total weight of the lipid phase, of one or more lipids which exhibit an interfacial tension towards water of less than about 20 mN/m.

6. The emulsion of claim 1, wherein the emulsion comprises both polar lipids and moderately polar lipids.

7. The emulsion of claim 1, wherein (a) comprises cocoglycerides.

8. The emulsion of claim 1, wherein (a) comprises dimethicone.

9. The emulsion of claim 1, wherein the emulsion further comprises at least one of cetyl alcohol, stearyl alcohol and cetearyl alcohol.

10. The emulsion of claim 1, wherein the emulsion comprises at least about 3% of the one or more polyols.

11. The emulsion of claim 1, wherein the emulsion comprises at least about 5% of the one or more polyols.

12. The emulsion of claim 1, wherein the one or more polyols comprise glycerin.

13. The emulsion of claim 1, wherein the emulsion is an O/W emulsion.

14. The emulsion of claim 13, wherein the O/W emulsion comprises one or more O/W emulsifiers selected from glyceryl stearate citrate, polyglyceryl methyl glucose distearate and polyethylene glycol(2000) monostearate.

15. An emulsion for making a cosmetic preparation, wherein the emulsion comprises (a) more than about 40% by weight, based on a total weight of a lipid phase of the emulsion, of at least one polar lipid and at least one moderately polar lipid which exhibit an interfacial tension towards water of less than about 30 mN/m, (b) one or more 1,2-alkanediols having from about 4 to about 8 carbon atoms and exhibiting an lg $p_{ow}$ of from about −1 to about +1, which 1,2-alkanediols comprise 1,2-hexanediol, and (c) from about 3% to about 30% by weight of one or more polyols, which polyols comprise glycerol, the emulsion being different from a microemulsion and being an oil-in-water (O/W) emulsion.

16. The emulsion of claim 15, wherein the emulsion comprises more than about 40% by weight, based on the total weight of the lipid phase, of one or more lipids which exhibit an interfacial tension towards water of less than about 20 mN/m.

17. The emulsion of claim 15, wherein (a) comprises cocoglycerides.

18. A cosmetic preparation which comprises the emulsion of claim 1.

19. The cosmetic preparation of claim 18, wherein the preparation is present as a cream, a lotion, or a pump spray.

20. A method of producing a cosmetic preparation which comprises a predominantly polar lipid phase and exhibits long-term stability, wherein the method comprises incorporating into the preparation an emulsion according to claim 1.

* * * * *